United States Patent [19]
Aberg et al.

[11] Patent Number: 5,736,577
[45] Date of Patent: *Apr. 7, 1998

[54] METHODS AND COMPOSITIONS FOR TREATING URINARY INCONTINENCE USING OPTICALLY PURE (S)-OXYBUTYNIN

[75] Inventors: Gunnar Aberg, Sarasota, Fla.; John R. McCullough, Worcester, Mass.

[73] Assignee: Sepracor, Inc., Marlborough, Mass.

[*] Notice: The term of this patent shall not extend beyond the expiration date of Pat. No. 5,532,278.

[21] Appl. No.: 671,976

[22] Filed: Jun. 28, 1996

Related U.S. Application Data

[63] Continuation-in-part of Ser. No. 381,542, Jan. 31, 1995, Pat. No. 5,532,278.
[51] Int. Cl.$^6$ .......................... A61K 31/165; A61K 9/70; A61K 9/66; A61K 9/46
[52] U.S. Cl. .......................... 514/617; 424/449; 424/451; 424/464; 424/310; 424/946
[58] Field of Search ........................ 514/617; 424/449, 424/451, 464, 946, 310

[56] References Cited

FOREIGN PATENT DOCUMENTS

| | | |
|---|---|---|
| 940540 | 7/1961 | United Kingdom. |
| 92/20377 | 5/1992 | WIPO. |

OTHER PUBLICATIONS

Lish et al. "Oxybutynin—A Musculotropic Antispasmodic Drug . . ." *Arch. int. Pharmacodyn.* 156, 456–488 (1965).
Hock "Clinical Evaluation of Oxybutynin Chloride" *Current Therapeutic Research* 9, 437–440 (1967).
Fredericks et al. "A Study of the Anticholinergic and Antispasmodic Activity of Oxybutynin . . ." *Investigative Urology* 12, 317–319 (1975).
Nilvebrant et al. "Dicyclomine, Benzhexol and Oxybutynine Distinguish . . ." *Europ. J. Pharmacol.* 123, 133–143 (1986).
Tonini et al. "Depressant Action of oxybutynin on the contractility . . ." *J. Pharm. Pharmacol.* 39, 103–107 (1986).
Kachur et al. "R and S Enantiomers of Oxybutynin: Pharmacological Effects . . ." *J. Pharm. Exper. Ther.* 247, 867–872 (1988).
Noronha–Blob et al. "Muscarinic Receptors: Relationships Among Phosphoinositude . . ." *J. Pharm Exper. Ther.* 249, 843–851 (1989).
Noronha–Blob et al. "The Anticholinergic Activity of Agents Indicated for Urinary . . ." *J. Pharm. Exper. Ther.* 251, 586–593 (1989).
Peterson et al. "In Vivo Crystometrogram Studies in Urethane–Anesthetized and Conscious Guinea Pigs" *J. Pharm. Methods* 21, 231–241 (1989).
Guarneri et al. "Effects of Oxybutynin, Terodiline, and Nifedipine . . ." *Pharm. Research* 24, 263–272 (1991).
Noronha–Blob et al. "Enantiomers of Oxybutynin: In Vitro Pharmacological Characterization . . ." *J. Pharm. Exp. Ther.* 256, 562–567 (1990).
Lowe et al. "Effect of extracellular $Ca^{2+}$ on cholinergic, KCl and phorbol ester–mediated . . ." *Eur. J. Pharm.* 195, 273–279 (1991).
Massad et al. "The Pharmacokinetics of Intravesical and Oral Oxybutynin Chloride" *J. Urology* 148, 595–597 (1992).
Angelico et al. "In Vivo Effects of Different Antispasmodic Drugs on the Rat Bladder Contractions" *J. Pharm. Methods* 27, 33–39 (1992).
Guarneri et al. "Effects of Drugs Used in the Therapy of Detrusor Hyperactivity . . ." *Pharm. Research* 27, 173–187 (1993).
Lindeke et al. "Metabolism of Oxybutynin: establishment of desethyloxybutynin and Oxybutynin N–Oxide formation in Rat Liver Preparations using Deuterium Substitution and Gas Chromatographic Mass Spectrometric Analysis" *Biomedical Mass Spectrometry*, vol. 8, No. 10, 506–513 (1981).
Kasama et al. "Preparation of Substituted Glycolic acid 4–alkyl–amino–2–butynyl Esters as Antispasmodics and for Regulation of Urination" *Chemical Abstracts*, vol. 113:23118k, 586 (1990).

*Primary Examiner*—John W. Rollins
*Attorney, Agent, or Firm*—Heslin & Rothenberg, P.

[57] ABSTRACT

A method for treating urinary incontinence while avoiding concomitant liability of adverse effects associated with racemic oxybutynin is disclosed. The method comprises administering a therapeutically effective amount of (S)-oxybutynin, or a pharmaceutically acceptable salt thereof, substantially free of its R enantiomer. Pharmaceutical compositions comprising (S)-oxybutynin, or a pharmaceutically acceptable salt thereof, substantially free of its R enantiomer, and a pharmaceutically acceptable carrier are also disclosed.

13 Claims, No Drawings

METHODS AND COMPOSITIONS FOR TREATING URINARY INCONTINENCE USING OPTICALLY PURE (S)-OXYBUTYNIN

CROSS-REFERENCE TO RELATED APPLICATIONS

This is a continuation-in-part of applicants' U.S. patent application Ser. No. 08/381,542, filed Jan. 31, 1995, now U.S. Pat. No. 5,532,278.

FIELD OF THE INVENTION

The invention relates to methods for treating urinary incontinence using optically pure (S)-oxybutynin and to pharmaceutical compositions containing optically pure (S)-oxybutynin.

BACKGROUND OF THE INVENTION

Racemic oxybutynin is used therapeutically in the treatment of intestinal hypermotility and in the treatment of urinary incontinence due to detrusor instability. Racemic oxybutynin exerts a direct antispasmodic effect on smooth muscle and inhibits the action of acetylcholine on smooth muscle. It exhibits only one-fifth of the anticholinergic activity of atropine on the rabbit detrusor muscle, but four to ten times the antispasmodic activity. It is quite selective for muscarinic receptors in the presence of nicotinic receptors and as a result, no blocking effects are observed at skeletal neuromuscular junctions or autonomic ganglia.

Racemic oxybutynin relaxes bladder smooth muscle and, in patients with conditions characterized by involuntary bladder contractions, cystometric studies have demonstrated that racemic oxybutynin increases vesicle capacity, diminishes the frequency of involuntary contractions of the detrusor muscle, and delays the initial desire to void. It is therefore useful in the treatment and prevention of both incontinency and frequent voluntary urination. The efficacy of racemic oxybutynin in the bladder has been attributed to a combination of antimuscarinic, direct spasmolytic and local anesthetic effects on the detrusor smooth muscle. Because of the antimuscarinic activity of the racemic drug, xerostomia (dry mouth) and mydriasis (dilated pupils), which involve muscarinic cholinergic receptors, are very common side effects. In fact, at least one researcher has referred to the "inevitable symptoms of mydriasis, xerostomia, tachycardia, etc." that accompany the administration of racemic oxybutynin [Lish et al. Arch. Int. Pharmacodyn., 156:467–488 (1965), 481]. The high incidence of anticholinergic side effects (40 to 80%) often results in dosage reduction or discontinuation of therapy.

Pharmacological studies of the individual enantiomers have suggested that the R-enantiomer is the efficacious enantiomer. Noronha-Blob et al. [J. Pharmacol. Exp, Ther., 256:562–567 (1991)] concluded that the cholinergic antagonism of racemic oxybutynin (measured in vitro by its affinity for $M_1$, $M_2$ and $M_3$ receptors subtypes and in vivo for diverse physiological responses) could be attributed mainly to the activity of the R-enantiomer. For all responses they found the rank order of potency of racemic oxybutynin and its enantiomers to be the same, namely, (R)-oxybutynin greater than or equal to racemic oxybutynin, which was much greater than (S)-oxybutynin, with (S)-oxybutynin being 1 to 2 orders of magnitude less potent than (R)-oxybutynin.

SUMMARY OF THE INVENTION

It has now been unexpectedly found that the substantially optically pure S enantiomer provides a superior therapy for the treatment of urinary incontinence.

Optically pure (S)-oxybutynin provides this treatment while substantially reducing the adverse effects that primarily arise from anticholinergic activity and that are associated with the administration of racemic oxybutynin. These include, but are not limited to, xerostomia, mydriasis, drowsiness, nausea, constipation, palpitations and tachycardia. The amelioration of cardiovascular side effects of racemic oxybutynin, such as tachycardia and palpitations, by the administration of (S)-oxybutynin is of particular therapeutic value.

The active compound of these compositions and methods is an optical isomer of oxybutynin. The preparation of racemic oxybutynin is described in British Patent Specification 940,540. Chemically, the active compound is the S enantiomer of 4-(diethylamino)-2-butynyl α-cyclohexyl-α-hydroxybenzeneacetate also known as 4-(diethylamino)-2-butynyl phenylcyclohexylglycolate, and hereinafter referred to as oxybutynin. The generic name given to the hydrochloride salt of racemic oxybutynin by the USAN Council is oxybutynin chloride; it is sold under the trade name of Ditropan®. The isomer of oxybutynin having the S absolute stereochemistry (Registry Number 119618-22-3) is dextrorotatory, and is shown in Formula I:

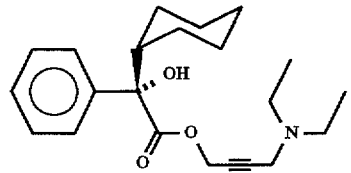

The synthesis of (S)-oxybutynin has been described [Kachur et al. J. Pharmacol. Exp. Ther., 247:867–872 (1988)], but (S)-oxybutynin itself is not presently commercially available. All of the clinical results that have been reported have been obtained with the racemic mixture, although the pharmacology of the individual enantiomers has been described in guinea pigs and rats [see Kachur et al. J. Pharmacol, Exp. Ther., 247:867–872 (1988) and Noronha-Blob et al. J. Pharmacol, Exp. Ther., 256:562–567 (1991)].

In one aspect the invention relates to a method for treating urinary incontinence while avoiding concomitant liability of adverse effects, which comprises administering to a human in need of such treatment a therapeutically effective amount of (S)-oxybutynin or a pharmaceutically acceptable salt thereof, substantially free of its R enantiomer. In another aspect, the present invention provides pharmaceutical compositions which comprise (S)-oxybutynin, or a pharmaceutically acceptable salt thereof, substantially free of (R)-oxybutynin, and a pharmaceutically acceptable carrier.

The term "substantially free of its R enantiomer" as used herein means that the compositions contain at least 90% by weight of (S)-oxybutynin and 10% by weight or less of (R)-oxybutynin. In a more preferred embodiment, the composition contains at least 99% by weight of (S)-oxybutynin and 1% or less (R)-oxybutynin.

The substantially optically pure (S)-oxybutynin may be administered parenterally, rectally, intravesically, transdermally, orally or by aerosol, orally and transdermally being preferred, at a rate of about 0.1 mg to about 1 gram per day, depending In another aspect, the invention relates to a pharmaceutical unit dosage form comprising (S)-oxybutynin, or a pharmaceutically acceptable salt thereof, substantially free of its (R) stereoisomer, and a pharmaceutically acceptable carrier in the form of a tablet, soft elastic gelatin capsule, or transdermal delivery device. For the tablet and soft elastic gelatin capsule forms, (S)-oxybutynin preferably is present in an amount of about 0.1 mg to 250 mg, and more preferably in an amount of about 0.25 mg to 100 mg, and even more preferably in an amount of about 0.5 mg to 25 mg, and are prepared by conventional methods, well-known in the art. The transdermal administration is improved by the inclusion of a permeation enhancer in the transdermal delivery device, for example as described in PCT application WO 92/20377.

DETAILED DESCRIPTION OF THE INVENTION

The S enantiomer of oxybutynin may be obtained by resolution of the intermediate mandelic acid followed by esterification as described by Kachur et al. (op. cit.). Alternatively, the S enantiomer may be obtained by the resolution of racemic oxybutynin using conventional means such as fractional crystallization of diastereomeric salts with chiral acids. Other standard methods of resolution known to those skilled in the art, including, but not limited to, simple crystallization and chromatography on a chiral substrate can also be used.

The magnitude of a prophylactic or therapeutic dose of (S)-oxybutynin in the acute or chronic management of disease will vary with the severity and nature of the condition to be treated and the route of administration. The dose and perhaps the dose frequency will also vary according to the age, body weight and response of the individual patient. In general, the total daily dose range for (S)-oxybutynin for the conditions described herein is from about 0.1 mg to about 1 gram, preferably from about 0.4 mg to about 500 mg, more preferably from about 0.7 mg to about 250 mg, and even more preferably from about 1 mg to 100 mg, in single or divided doses, preferably in divided doses. In managing the patient, the therapy should be initiated at a lower dose, perhaps at about 0.25 mg to about 25 mg, and increased depending on the patient's global response, e.g., up to about 100 mg. It is further recommended that patients over 65 years and those with impaired renal or hepatic function initially receive low doses and that they be titrated based on individual response(s) and blood level(s). It may be necessary to use dosages outside these ranges in some cases, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat incontinence but insufficient to cause adverse effects" are encompassed by the above-described dosage amounts and dose frequency schedule.

Any suitable route of administration may be employed for providing the patient with an effective dosage of (S)-oxybutynin. For example, oral, rectal, parenteral (subcutaneous, intramuscular, intravenous), transdermal, aerosol and like forms of administration may be employed. Additionally, the drug may be administered directly into the bladder through the urethra, as described for racemic oxybutynin by Massad et al. [*J. Urol.*, 148:595–597 (1992)]. Dosage forms include tablets, troches, dispersions, suspensions, solutions, capsules, transdermal delivery systems, and the like.

The pharmaceutical compositions of the present invention comprise (S)-oxybutynin as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids. Suitable pharmaceutically acceptable acid addition salts for the compound of the present invention include acetic, benzene- sulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. The hydrochloride has particular utility and was, in fact, the salt used in the studies described below.

The compositions of the present invention include suspensions, solutions, elixirs, or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations.

Because of their ease of administration, tablets and capsules represent one of the more advantageous oral dosage unit forms, in which case solid pharmaceutical carriers are employed. If desired, tablets may be coated by standard aqueous or nonaqueous techniques.

In a preferred embodiment, the pharmaceutical compositions of the present invention may be formulated in a soft elastic gelatin capsule unit dosage form by using conventional methods, well-known in the art (see, e.g., Ebert, *Pharm. Tech.*, 1(5):44–50(1977)). Soft elastic gelatin capsules have a soft, globular, gelatin shell somewhat thicker than that of hard gelatin capsules, wherein a gelatin is plasticized by the addition of glycerin, sorbitol, or a similar polyol. The hardness of the capsule shell may be changed by varying the type of gelatin and the amounts of plasticizer and water. The soft gelatin shells may contain a preservative to prevent the growth of fungi, such as methyl- and propylparabens and sorbic acid. The active ingredient may be dissolved or suspended in a liquid vehicle or carrier, such as vegetable or mineral oils, glycols such as polyethylene glycol and propylene glycol, triglycerides, surfactants such as polysorbates, or a combination thereof. In the soft elastic gelatin capsule pharmaceutical unit dosage form of the present invention, (S)-oxybutynin is preferably present in an amount of about 0.1 mg to about 250 mg, more preferably in an amount of about 0.25 mg to about 100 mg, and even more preferably in an amount of about 0.5 mg to about 25 mg.

In addition to the common dosage forms set out above, the compounds of the present invention may also be administered by controlled release means and delivery devices such as those described in U.S. Pat. Nos.: 3,845,770; 3,916,899; 3,536,809; 3,598,123; and 4,008,719, and PCT application WO 92/20377.

Pharmaceutical compositions of the present invention suitable for oral administration may be presented as discrete units such as capsules, cachets, or tablets, each containing a predetermined amount of the active ingredient, as a powder or granules, or as soft elastic gelatin capsules wherein the active ingredient is dissolved or suspended in a liquid carrier, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation, just as is known for the racemic mixture.

The surprising utility of the S enantiomer has been established by the following studies.

Binding of (R)- and (S)-Oxybutynin to Human $M_1$, $M_2$, $M_3$, and $M_4$ Muscarinic Receptors Protein Source The experiments were carried out on membranes prepared from SF9 cells infected with baculovirus to express the human recombinant $M_1$, $M_2$, $M_3$, and $M_4$ muscarinic receptor subtypes.

Binding Assays

| Receptor | Radioligand | Conc. | Nonspecific | Incubation | Reference Compound |
|---|---|---|---|---|---|
| $M_{1H}$ | [$^3$H] pirenzepine | 2 nM | atropine (1 μM) | 60 min/27° C. | pirenzepine |
| $M_{2H}$ | [$^3$H] AF-DX 384 | 2 nM | atropine (1 μM) | 60 min/27° C. | methoctramine |
| $M_{3H}$ | [$^3$H] 4-DAMP | 0.8 nM | atropine (1 μM) | 60 min/27° C. | 4-DAMP |
| $M_{4H}$ | [$^3$H] 4-DAMP | 0.3 nM | atropine (1 μM) | 60 min/27° C. | 4-DAMP |

Following incubation, the assays were rapidly filtered under vacuum through GF/B glass fiber filters (Whatman) and washed with an ice-cold buffer using a Brandel Cell Harvester. Bound radioactivity was determined with a liquid scintillation counter (LS 6000, Beckman) using a liquid scintillation cocktail (Formula 99, DuPont NEN).

Experimental Protocol

The compounds were tested on each receptor at 10 concentrations in duplicate to obtain competition curves. In each experiment, the reference compound for the receptor under investigation was simultaneously tested at 8 concentrations in duplicate to obtain a competition curve in order to validate this experiment.

Analysis and Expression of Results

The specific radioligand binding of each receptor was defined as the difference between total binding and nonspecific binding determined in the presence of an excess of unlabelled ligand. $IC_{50}$ values (concentrations required to inhibit 50% of specific binding) were determined by non linear regression analysis of the competition curves. These parameters were obtained by curve fitting using Sigmaplot™ software.

TABLE 1

Binding of R-oxybutynin and S-oxybutynin to Human Muscarinic Subtypes $M_1$–$M_4$

| Receptor | R-OXY $IC_{50}$ (nM) | S-OXY $IC_{50}$ (nM) | Ref. Compound | $IC_{50}$ (nM) |
|---|---|---|---|---|
| $M_1$ | 0.99 | 47.6 | Pirenzepine | 11.9 |
| $M_2$ | 9.9 | 178 | Methoctramine | 14.6 |
| $M_3$ | 1.8 | 149 | 4-DAMP | 1.6 |
| $M_4$ | 1.2 | 100 | 4-DAMP | 0.87 |

Binding of (R)- and (S)-Oxybutynin to Calcium Channels Binding assays

Binding assays were performed using the following methods:

| Receptors | Membranes | Reference Compounds | References |
|---|---|---|---|
| Ca channel (T + L, diltiazem site) | rat cerebral cortex | diltiazem | Schoemaker and Langer (1985) |
| Ca channel (T + L verapamil site) | rat cerebral cortex | D600 | Reynolds et el (1986) |

The experiment conditions were:

| Receptors | Ligands | Concentrations | Nonspecific | Incubation |
|---|---|---|---|---|
| Ca channel (T + L, diltiazem site) | [$^3$H] diltiazem | 5 nM | dilitiazem (10 mM) | 120 min/25° C. |
| Ca channel (T + L, verapamil site) | [$^3$H] D 888 | 0.5 nM | D 600 (10 mM) | 60 min/22° C. |

Following incubation, the assays were rapidly filtered under vacuum through GF/B or GF/C glass fiber filters (Whatman) and washed with an ice-cold buffer using a Brandel Cell Harvester. Bound radioactivity was determined with a liquid scintillation counter (LS6000, Beckman) using a liquid scintillation cocktail (Formula 989, DuPont NEN).

Experimental Protocols

The compounds were tested in duplicate on each receptor at a concentration of $10^{-5}$M. In each experiment, the reference compound for the receptor under investigation was simultaneously tested at 8 concentrations in duplicate to obtain a competition curve in order to validate this experiment.

Analysis and Expression of Results

The specific radioligand binding of each receptor was defined as the difference between total binding and nonspecific binding determined in the presence of an excess of unlabelled ligand. Mean values, expressed as a percentage of inhibition of specific binding, are presented in Table 2. $IC_{50}$ values (concentration required to inhibit 50% of specific binding) were determined by non linear regression analysis of their competition curves. These parameters were obtained by curve fitting using Sigmaplot™ software.

TABLE 2

Binding of R-oxybutynin and S-oxybutynin to Calcium Channels
[Inhibition (in %) of diltiazem and verapmil binding to calcium channel receptors.]

| Receptor | R-OXY ($10^{-5}$ M) | S-OXY ($10^{-5}$ M) | Ref. Compound | $IC_{50}$ (nM) |
|---|---|---|---|---|
| Calcium (diltiazem) | 86 | 59 | diltiazem | 55.8 |
| Calcium (verapamil) | 86 | 68 | D600 | 36.4 |

While it is well known that the normal emptying of the bladder is mediated through cholinergic mechanisms, the bladder instability that is seen in patients suffering from incontinence appears to be related to non-cholinergic contractions of the bladder. Andersson et al. [*Neurourol Urodyn,* 5:579–586 (1986)] have shown in animals that the atropine-resistant detrusor muscle is highly sensitive to calcium antagonists.

The study of the receptor binding affinity of (R)- and (S)-oxybutynin to the receptor sites for the calcium channel blockers diltiazem and verapamil described above allows one to conclude that S-oxybutynin has therapeutic effects on involuntary micturition, while this isomer (contrary to the R-isomer and the racemate) has very little effect on the normal voiding mechanism and also has significantly decreased anticholinergic side effects as compared with the R-isomer and racemate. The avoidance of cardiovascular side effects that arise from the anticholinergic action of racemic oxybutynin is of particular note.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference.

What is claimed is:

1. A method for treating urinary incontinence which comprises administering to a human in need thereof a therapeutically effective amount of (S)-oxybutynin, or a pharmaceutically acceptable salt thereof, substantially free of (R)-oxybutynin, wherein the amount of (S)-oxybutynin, or a pharmaceutically acceptable salt thereof, administered is from about 0.1 mg to about 1 gram per day.

2. The method according to claim 1, wherein the amount of (S)-oxybutynin, or a pharmaceutically acceptable salt thereof, administered is from about 0.4 mg to about 500 mg per day.

3. The method according to claim 2, wherein the amount of (S)-oxybutynin, or a pharmaceutically acceptable salt thereof, administered is from about 0.7 mg to about 250 mg per day.

4. The method according to claim 1, wherein (S)-oxybutynin, or a pharmaceutically acceptable salt thereof, is administered by inhalation or by parenteral, transdermal, rectal or oral administration.

5. The method according to claim 4, wherein (S)-oxybutynin, or pharmaceutically acceptable salt thereof, is administered by oral administration.

6. A pharmaceutical composition comprising (S)-oxybutynin, or a pharmaceutically acceptable salt thereof, substantially free of (R)-oxybutynin, and a pharmaceutically acceptable carrier.

7. The pharmaceutical composition according to claim 6, wherein said pharmaceutical composition contains at least 99% by weight (S)-oxybutynin and 1% or less by weight (R)-oxybutynin.

8. A pharmaceutical unit dosage form which comprises (S)-oxybutynin, or a pharmaceutically acceptable salt thereof, substantially free of (R)-oxybutynin, and a pharmaceutically acceptable carrier in the form of a soft elastic gelatin capsule.

9. The pharmaceutical unit dosage form according to claim 8, wherein (S)-oxybutynin, or a pharmaceutically acceptable salt thereof, is present in an amount of about 0.1 mg to about 250 mg.

10. The pharmaceutical unit dosage form according to claim 9, wherein (S)-oxybutynin, or a pharmaceutically acceptable salt thereof, is present in an amount of about 0.25 mg to about 100 mg.

11. The pharmaceutical unit dosage form according to claim 10, wherein (S)-oxybutynin, or a pharmaceutically acceptable salt thereof, is present in an amount of about 0.5 mg to about 25 mg.

12. A pharmaceutical unit dosage form which comprises (S)-oxybutynin, or a pharmaceutically acceptable salt thereof, substantially free of (R)-oxybutynin, and a pharmaceutically acceptable carrier in the form of a tablet, wherein (S)-oxybutynin is present in an amount of about 0.1 mg to about 250 mg.

13. The pharmaceutical unit dosage form according to claim 12, wherein (S)-oxybutynin, or a pharmaceutically acceptable salt thereof, is present in an amount of about 0.25 mg to about 100 mg.

* * * * *